United States Patent [19]

Gutman et al.

[11] Patent Number: 5,599,929
[45] Date of Patent: Feb. 4, 1997

[54] METHOD FOR PREPARING OPIPRAMOL

[75] Inventors: Daniella Gutman, Rishon Lezion; Mishel Ashkar, De'er Hanna, both of Israel

[73] Assignee: Taro Pharmaceutical Industries Ltd, Haifa Bay, Israel

[21] Appl. No.: 336,837

[22] Filed: Nov. 9, 1994

[51] Int. Cl.$^6$ ............... C07D 223/24; C07D 403/06
[52] U.S. Cl. ................................. 540/592; 540/588
[58] Field of Search ............................... 540/592

[56] References Cited

U.S. PATENT DOCUMENTS

| | | | |
|---|---|---|---|
| 2,965,639 | 12/1960 | Schindler | 260/239 |
| 3,317,515 | 5/1967 | Paquette | 260/239 |
| 3,668,210 | 6/1972 | Nakanishi et al. | 260/293.59 |
| 3,679,662 | 7/1972 | Morita et al. | 260/239 D |

FOREIGN PATENT DOCUMENTS

| | | |
|---|---|---|
| 73098 | 9/1960 | France . |
| 1133729 | 7/1962 | Germany . |

OTHER PUBLICATIONS

S. J. Schmolka et al., *N–Dimethylaminopropylation in a Solid–Liquid Two Phase System: Synthesis of Chlorpromazine, its Analogs, and Related Compounds*, Synthesis, No. 1, Stuttgart, Germany, Jan. 1984, pp. 29–31.

Leo A. Paquette, Hydroxylamine Chemistry. V. O–(2–Hydroxyethyl) acetone Oxime p–Toluenesulfonate, a Useful Intermediate for the Preparation of Hydroxylamine Derivatives, 1964, vol. 29, pp. 3545–3548 month of publication not provided.

E. D. Bergmann et al., Some Derivatives of 5H–Dibenz[b.f] Azepine, Tetrahedron, 1968, vol. 24, pp. 1289–1292. month of publication not provided.

L. J. Kricka et al., Reactions of Condensed N–Heteroaromatic Molecules. J. Chem. Soc., 1972, pp. 2292–2293 month of publication not provided.

Gozlan, I. et al. *J. Heterocycl. Chem.* 19, 1569–1571 (1982).
Hannig, E. *Pharmazie* 34, 670–671 (1979). CA Abstract No. 93:26248.

*Primary Examiner*—Mukund J. Shah
*Assistant Examiner*—King Lit Wong
*Attorney, Agent, or Firm*—Michael A. Gollin; Spencer & Frank

[57] ABSTRACT

An improved method for preparing opipramol (I) is disclosed, wherein iminostilbene (II) is reacted with 1-bromo-3-chloropropane in the presence of a weak base selected from a hydrogen phosphate salt and an acetate salt and in the presence of a phase transfer agent to produce N-(3-halopropyl)iminostilbene (III), which is mixture of N-(3-chloropropyl)iminostilbene and N-(3-bromopropyl)iminostilbene, and then N-(3-halopropyl)iminostilbene is reacted with N-(2-hydroxyethyl)piperazine to form opipramol, as shown in the following equations, where X is chlorine or bromine.

10 Claims, No Drawings

METHOD FOR PREPARING OPIPRAMOL

BACKGROUND OF INVENTION

This invention is concerned with a novel and improved method for preparing the antipsychotic and antidepressant drug, opipramol (I). More particularly, this invention is concerned with a novel method for converting iminostilbene (II), also known as dibenzo-[b,f]azepine, into N-(3-halopropyl)iminostilbene, a mixture of 3-chloro- and 3-bromopropyl derivatives, which is a precursor one step removed from opipramol (I).

In a preferred method of synthesizing opipramol (I), iminostilbene (II) is used as the starting material and is first alkylated with 1-bromo-3-chloropropane to yield N-(3-halopropyl)-iminostilbene (III), which is used in turn to alkylate N-(2-hydroxyethyl)piperazine at the secondary amine site to yield opipramol(I), as shown by the following equations, where X is chlorine or bromine.

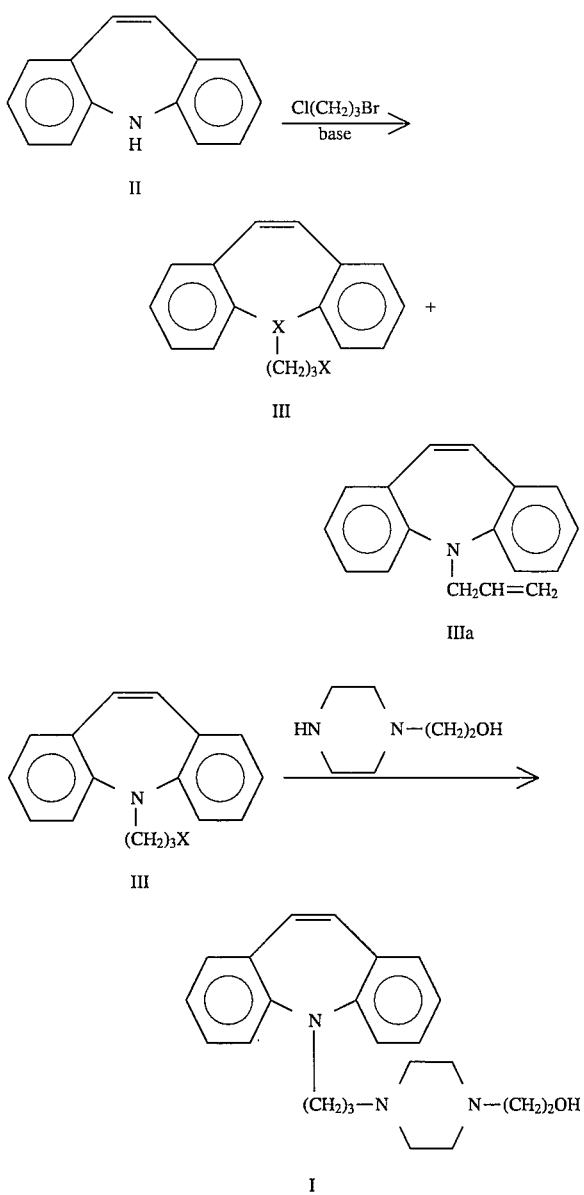

According to German Patent 1133729, alkylation of iminostilbene (II) requires the use of a strong base catalyst, such as sodamide. Sodamide has been employed in non-aqueous media, to convert iminostilbene (II) into its anion (V), which may then be alkylated, a shown by the equations below.

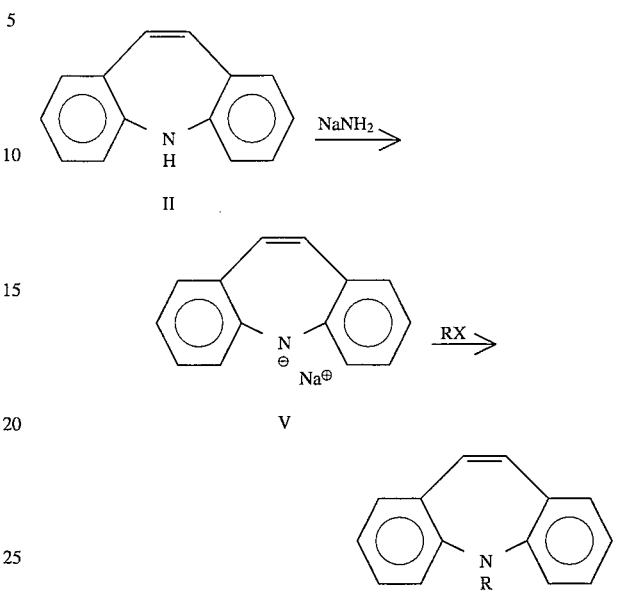

where R is lower alkyl and X is halogen, preferably Br.

When R is free of base-sensitive groups, such a procedure is effective and efficient. However, when 1-bromo-3-chloropropane is the alkylating reagent, the desired product, N-(3-halopropyl)-iminostilbene (III) is converted by the strongly basic medium, at least in part, to the illustrated dehydrohalogenated by-product, N-allyl-iminostilbene (IIIa), which is unsuitable for direct conversion to opipramol (I).

SUMMARY OF THE INVENTION

The object of this invention is a new and improved method for the preparation of opipramol.

Another object of the invention is a new and improved method for the preparation of the immediate precursor, N-(3-halopropyl)-iminostilbene, in the preparation of opipramol.

These and other objects are achieved by the invention described below.

Surprisingly, it has been discovered that alkylation of iminostilbene (II) can be carried out with excellent results using a weak base, selected from a phosphate of the formula, $M_xHPO_4$ (IV), or an acetate of the formula, $CH_3COOM$ (IVa), wherein M is an alkali metal, alkaline earth metal or ammonium and x is 1 or 2, determined by the valence of M. Desirably, the alkylation is also carried out in the presence of a phase transfer agent.

According to the invention, iminostilbene (II) is alkylated with 1-bromo-3-chloropropane in the presence of a weak base of the formula $MxHPO_4$ (IV) or $CH_3COOM$ (IVa), where M and x are as defined above, and a phase transfer agent, and the resultant N-(3-halopropyl)iminostilbene (III) is reacted with N-(2-hydroxyethyl)-piperazine to yield opipramol (I).

DESCRIPTION OF THE INVENTION

With the use of the weak base $M_xHPO_4$ (IV) or $CH_3COOM$ (IVa) and phase transfer agent, the undesirable

3 elimination of HX from N-(3-halopropyl)iminostilbene (III) does not occur, thereby increasing the net yield of N-(3-halopropyl)iminostilbene (III), improving the efficiency of the process and avoiding the necessity of removing unwanted by-product.

As the weak base, phosphate salts (IV) are preferred and M is preferably sodium, potassium or ammonium in formulas (IV) and (Iva).

According to the invention, the action of $M_xHPO_4$ (IV) and $CH_3COOM$ (IVa) is best achieved by heating the reactants in a solvent in the presence of a phase transfer agent. Useful phase transfer agents include quaternary ammonium salts; aryltrialkylammonium salts, such as benzyltriethylammonium chloride, are preferred. The phase transfer agent is used in a catalytically effective amount, preferably 3–10% by weight, based on the weight of iminostilbene.

Solvents suitable for the first step of the process include those substantially inert to the reagents of the reaction, which include alkylbenzenes, such as toluene, and also dimethylformamide, dimethylacetamide, isopropanol, butanol, and diethylene glycol; alkylbenzenes and particularly toluene are preferred. The alkylation is preferably carried out at a temperature of 80°–140° C., most preferably at 110° C.

1-Bromo-3-chloropropane and the weak base (IV) or (IVa) are each used in approximately stoichiometric equivalents or in excess of the amount required to alkylate iminostilbene (II). The product of this alkylation, N-(3-halopropyl)iminostilbene (III), is a mixture of N-(3-bromopropyl)iminostilbene and N-(3-chloropropyl)iminostilbene; the particular proportion of 3-chloro- and 3-bromopropyl derivatives is of no importance, since both compounds are readily converted to opipramol (I) by reaction with N-[2-hydroxyethyl]-piperazine.

In a preferred embodiment of the invention, the first step of the process is carried out by heating a solution of iminostilbene (II) containing 1-bromo-3-chloropropane and disodium hydrogen phosphate in the presence of a catalytic amount of benzyltriethylammonium chloride. After removal of salts by washing and any excess unreacted 1-bromo-3-chloropropane by co-distillation with a higher boiling solvent, N-(3-halopropyl)iminostilbene (III) in the resultant solution is converted without further isolation into opipramol (I) by reaction in situ with N-[2-hydroxyethyl]-piperazine.

The reaction of N-(3-halopropyl)iminostilbene (III) with N-[2-hydroxyethyl]-piperazine is preferably carried out with an excess of N-[2-hydroxyethyl]-piperazine at a temperature of about 50° to 150° C., most preferably at about 110° C., in the presence of a base until the alkylation is substantially complete. The mole ratio of N-(3-halopropyl)iminostilbene (III) to N-[2-hydroxyethyl]-piperazine is preferably about 1:1 to 1:3 and most preferably about 1:2. A weak base, such as sodium carbonate or potassium carbonate is preferred and is used in amount effective to achieve reaction between iminostilbene (III) and N-[2-hydroxyethyl]-piperazine.

The following examples further illustrate the best mode currently contemplated for carrying out the invention, but the illustrative examples must not be construed as limiting the invention in any manner.

4

EXAMPLE 1

Preparation of N-(3-Halopropyl)iminostilbene (III)

To a stirred solution of 360 g (2,185 moles) of 1-bromo-3-chloropropane in 750 ml of toluene, 150 g (0.777 moles) of iminostilbene (I), 270 g (1.9 moles) of disodium hydrogen phosphate and 7.5 g of benzyltriethylammonium chloride are added. The resulting mixture is heated to reflux until the reaction is substantially complete, which requires about 18 hours, as shown by tlc (petroleum ether: ether, 96:4); about 95% of iminostilbene (I) is consumed.

After the reaction mixture is cooled to room temperature, solids are removed from the reaction mixture by filtration and washed with toluene. The toluene and excess 1-bromo-3-chloropropane are removed by distillation under vacuum to a temperature of about 100° C.; 150 ml of Isopar G, a high boiling hydrocarbon, are added to the residue and distillation under vacuum is continued to about 100° C. The residue is cooled and 450 ml of toluene are added to provide a crude solution of N-(3-halopropyl)iminostilbene (III).

EXAMPLE 2

Preparation of Opipramol (I)

N-(3-halopropyl)iminostilbene (III) in a toluene solution, as prepared in Example 1, in an amount of 600 ml is mixed with 150 g of N-(2-hydroxyethyl)piperazine and 50 g of sodium carbonate and then heated slowly to 110° C., while $CO_2$ evolves. The reaction mixture is heated to reflux for another 16 hours, after which the mixture is cooled to 80° C.; 400 ml water are added, mixed and then separated from the toluene layer. The toluene layer is cooled to 30°–40° C. and 500 ml of a 1.5N aqueous solution of HCl or $H_2SO_4$ is mixed with the toluene layer; the aqueous layer is separated; the extraction is repeated with an additional 100 ml of the acidic solution and the aqueous extracts are combined. Toluene in an amount of 600 ml is added to the combined aqueous extracts; the mixture is heated to 50° C. and ammonium or sodium hydroxide is added until a pH≧9. The mixture is agitated for ½ hour at 60°–70° C., after which the toluene layer is separated and washed with 100 ml of water and then dried by azeotropic distillation. The toluene layer is then cooled to 0°–10° C. and centrifuged to obtain the solid products opipramol (I). Additional product is obtained by concentrating the toluene residue to about ¼ of its initial volume and cooling to 0°–10° C. The total amount of product obtained is 215 g, having a m.p. of 96° C.

Opipramol (I) can be further purified by dissolving 200 g of the above-obtained opipramol (I) in 600 ml of acetone; mixing 7 g of active carbon and 5 g of Celite into the solution, filtering and then cooling the solution to 0°–10° C. and finally collecting the purified product on a centrifuge. The m.p. of the purified product is 101° C.

What we desire to claim and protect by Letters Patent is:
1. A process for the preparation of opipramol comprising reacting iminostilbene with 1-bromo-3-chloropropane in the presence of a weak base selected from a hydrogen phosphate salt of the formula $M_xHPO_4$ and an acetate salt of the formula $CH_3COOM$, wherein M is an alkali metal, alkaline earth metal or ammonium and x is 1 or 2 depending on the valence of M, in the presence of a catalytically effective amount of a compatible phase transfer agent and in a solvent inert to the reagents in the reaction, to form a N-(3-halopropyl)iminostilbene, which is a a mixture of N-(3-bromopropyl)iminostilbene and N-(3-chloropropyl)iminostilbene;

separating any unreacted 1-bromo-3-chloropropane and any salt present from the reaction mixture;

reacting the thus formed N-(3-halopropyl)iminostilbene in situ, without isolation from the reaction mixture, with N-(2-hydroxyethyl)piperazine in the presence of a base to form opipramol and separating opipramol from the reaction mixture.

2. The process according to claim 1 wherein the weak base is a hydrogen phosphate salt of the formula $Na_2HPO_4$ or $K_2HPO_4$.

3. The process according to claim 1 in which the phase transfer agent is a quaternary ammonium chloride.

4. The process according to claim 1 in which the phase transfer agent is benzyltriethylammonium chloride.

5. The process according to claim 1 in which the reaction of iminostilbene with 1-bromo-3-chloropropane is carried out at a temperature of about 80°–140° C.

6. The process according to claim 1 in which said 1-bromo-3-chloropropane and said weak base are each present in an amount equal to or greater than their stoichiometric equivalents based on the amount of iminostilbene in the reaction.

7. The process according to claim 1 in which the reaction of iminostilbene with 1-bromo-3-chloropropane is carried out at a temperature of about 80°–140° C., the hydrogen phosphate salt is $Na_2HPO_4$ or $K_2HPO_4$, the phase transfer agent is benzyltriethyammonium chloride and the solvent is toluene.

8. The process according to claim 1 in which the reaction of N-(3-halopropyl)-iminostilbene with N-(2-hydroxyethyl)-piperazine is carried out with an excess of N-(2-hydroxyethyl)-piperazine at a temperature of about 50° to 150° C. in the presence of a weak base.

9. The process according to claim 1 in which the phase transfer agent is a quaternary ammonium salt.

10. The process according to claim 1 in which the mixture of N-(3-halopropyl) iminostilbene formed by the first reaction step is essentially free of N-allyl-iminostilbene.

\* \* \* \* \*